US009625399B2

(12) United States Patent
Zuñiga Escobar

(10) Patent No.: US 9,625,399 B2
(45) Date of Patent: Apr. 18, 2017

(54) DEVICE FOR DETERMINING THERMAL CONDUCTIVITY AND METHODS FOR THE USE THEREOF

(75) Inventor: Orlando Zuñiga Escobar, Santiago de Cali (CO)

(73) Assignee: UNIVERSIDAD DEL VALLE, Santiago de Cali (CO)

( * ) Notice: Subject to any disclaimer, the term of this patent is extended or adjusted under 35 U.S.C. 154(b) by 292 days.

(21) Appl. No.: 13/131,353

(22) PCT Filed: Dec. 1, 2009

(86) PCT No.: PCT/IB2009/055449
§ 371 (c)(1),
(2), (4) Date: Aug. 19, 2011

(87) PCT Pub. No.: WO2010/064196
PCT Pub. Date: Jun. 10, 2010

(65) Prior Publication Data
US 2011/0299563 A1    Dec. 8, 2011

(30) Foreign Application Priority Data

Dec. 2, 2008 (CO) .................................. 08 128174

(51) Int. Cl.
*G01N 25/18* (2006.01)
*G01N 33/24* (2006.01)

(52) U.S. Cl.
CPC ....... *G01N 25/18* (2013.01); *G01N 2033/245* (2013.01)

(58) Field of Classification Search
CPC ........ G01N 25/18; G01N 27/18; G01N 30/66; G01N 3/18; G01N 2203/0071;
(Continued)

(56) References Cited

U.S. PATENT DOCUMENTS 3,263,485 A    8/1966  Mahmoodi
3,592,060 A *  7/1971  Laverman ...................... 374/43
(Continued)

FOREIGN PATENT DOCUMENTS

ES    2259498    * 10/2006

OTHER PUBLICATIONS

Royer et al. "Soil Fertility Levels as Influenced by Long-time Differential Fertilization Practices", Aug. 1948, p. 685.*
(Continued)

*Primary Examiner* — Lisa Caputo
*Assistant Examiner* — Janice M Soto
(74) *Attorney, Agent, or Firm* — Mark T. Vogelbacker; Reed Smith LLP

(57) ABSTRACT

The application relates to a device based on the electrothermal method for determining thermal conductivity, which allows the examination of various phenomena, with a high level of reliability, through the study of the thermal behavior of materials. The device is constituted by a sample-carrying cylinder surrounded by a resistance element that creates a radial heat flow in the sample, a cooling system based on a spiral-form heat exchanger incorporated into the thermal device, means for the storage of a fluid and a data-storage device. Furthermore, the present application describes the use of the device in processes for determining the productive potential of the soil ("PPS") and the examination of the nutritional quality of agro-ecological produce and foods.

18 Claims, 5 Drawing Sheets

(58) Field of Classification Search
CPC .... G01N 2203/0222; G01N 3/08; G01N 3/14; G01N 25/20; F28F 2200/005; F28D 15/02; G01K 1/14; G01K 7/42; G01K 1/16; G01K 13/02; G01K 7/04; G01K 7/02; G01K 7/021; F25D 29/005
USPC .................................... 374/44, 141, 179, 50
See application file for complete search history.

(56) References Cited

U.S. PATENT DOCUMENTS

| | | | |
|---|---|---|---|
| 4,861,167 A | | 8/1989 | Lobo |
| 4,929,089 A | * | 5/1990 | Tsuchida .................. 374/44 |
| 6,142,662 A | * | 11/2000 | Narh et al. .................. 374/44 |
| 6,331,075 B1 | * | 12/2001 | Amer et al. ................. 374/44 |
| 7,540,656 B1 | * | 6/2009 | Stochl et al. ................. 374/29 |

OTHER PUBLICATIONS

Porta, C. J., López-Acevedo, R. M. y Roquero, C. Edafología para la agricultura y el medio ambiente. Ed. Mundi-Prensa, Madrid, España, 1994.

Montenegro y Malagón. Propiedades físicas de los suelos, 2 ed. IGAC, Bogotá D.C. Colombia, 1990.

Honorato, R. Manual de Edafología. Alfaomega 4ª edición. Universidad Católica de Chile, 2000.

Jury, W.A. and Roth, K. Transfer functions and solute movement through soil. Theory and applications. 1 ed. Basel: Birkhäuser Verlag Basel, p. 226, 1990.

Baver, L.D.; Gardner, W.H.; Gardner, W.R. Física de suelos. (Traducción de 4. ed. Soil Physiscs, New York: John Wiley and Sons Inc., 1972) 1 ed. en español. México: Unión Tipográfica Editorial Hispano-Americana U.T.E.H.A., Avenida Universidad, 767, México 12 ,D.F., 1973.

* cited by examiner

DEVICE FOR DETERMINING THERMAL CONDUCTIVITY AND METHODS FOR THE USE THEREOF

RELATED APPLICATIONS

This application is the United States National Stage of International Application No. PCT/IB2009/055449, filed Dec. 1, 2009, which was published as International Publication No. WO 2010/064196, and which claims benefit of Colombian Patent Application No. 8 128174 filed Dec. 2, 2008. Both applications are incorporated by reference in their entirety herewith.

FIELD OF THE INVENTION

The current invention is related to a device for the determination of thermal conductivity and its application in processes to determine the Productive Potential of Soil (PPS), analysis of the nutritional quality of foods and agro-ecological products.

BACKGROUND OF THE INVENTION

The thermal properties of the soil (calorific capacity, specific heat, thermal conductivity, and thermal diffusiveness) vary with water content, granulometry, and aggregation of the soil (Porta, C. J., López-Acevedo, R. M. y Roquero, C. Edafología para la agricultura y el medio ambiente. Ed. Mundi-Prensa, Madrid, España, p. 807, 1994) and are related with microbial activity, mineralization, and humification of the organic matter (Montenegro y Malagón. Propiedades fisicas de los suelos, 2 ed. IGAC, Bogotá D.C. Colombia, p. 813, 1990).

The thermal conductivity ($\lambda$) or ability of the soil to transfer heat through molecular conduction is expressed in calories flowing through a soil plate with unitary thickness and area, with a difference of 1° C. between the two faces (Honorato, R. Manual de Edafología. Alfaomega $4^a$ edición. Universidad Católica de Chile, p. 267, 2000). When the thermal conductivity of a soil is high, the temperature variations on the surface are lower. The thermal conductivity is increased with the humidity content, affecting also the changes of soil temperature; however, when there is saturation of the pores, it does not increase in the expected proportions. Thermal conductivity is considered a characteristic sensitive to changes operating on the soil (Honorato, R. Manual de Edafología. Alfaomega $4^a$ edición. Universidad Católica de Chile, p. 267, 2000; Jury, W. A. and Roth, K. Transfer functions and solute movement through soil. Theory and applications. 1 ed. Basel: Birkhäuser Verlag Basel, p. 226, 1990).

Numerous devices to determine thermal conductivity are known in literature, for example U.S. Pat. No. 4,861,167 presents an apparatus to determine thermal conductivity of fused polymers from the rate of temperature change in the sample. The apparatus is made up of an elongated cylindrical container that holds the sample, heating means located around the container, a temperature sensor, a probe that can inserted into the container which contacts the sample and which has a hollow needle, a heating medium and a sensor located on the body of the needle and means connected to the sensor to determine the change in temperature in the sample that is in contact with the probe. Also, U.S. Pat. No. 3,263,485 shows an apparatus to determine the thermal conductivity of a solid material through a method that compares the unknown value of conductivity of a sample against a material of known low thermal conductivity; the apparatus has a covered receptacle on the internal walls by isolating material, a cylindrical tube mounted inside the receptacle, a source of heat placed on one of the extremes of the tube, a plurality of heating wires rolled helicoidally on a corrugated surface on the external wall of the tube, and sensors to measure the temperature in fixed points of each of the samples.

In spite of the existence of the previously described, there is still the need for a device to directly determine the thermal conductivity of a solid sample like the soil (and not comparatively) during a relatively short processing time and based on a reliable methodology stemming from exactness and precision of the method.

The device to determine thermal conductivity of the invention is based on the thermo-electric method, which permits studying diverse phenomena with a high range of reliability through the thermal behavior of materials, solving the drawbacks of the previous art by means of a device constituted by a sample holder cylinder surrounded by a resistance that creates a radial flow of heat on the sample and a refrigeration system based on a heat exchanger in spiral shape integrated to the thermal device. This refrigeration system based on a heat exchanger in spiral form integrated to the device diminishes the processing time for each sample, increasing the number of determinations of thermal conductivity per unit of time; for which when increasing the efficiency in the process, there is also an increase in the number samples analyzed by the object of study offering greater information of such. Additionally, this device can be used for the analysis of the organic quality of foods and agricultural products.

OBJECTS OF THE INVENTION

Figure 1:
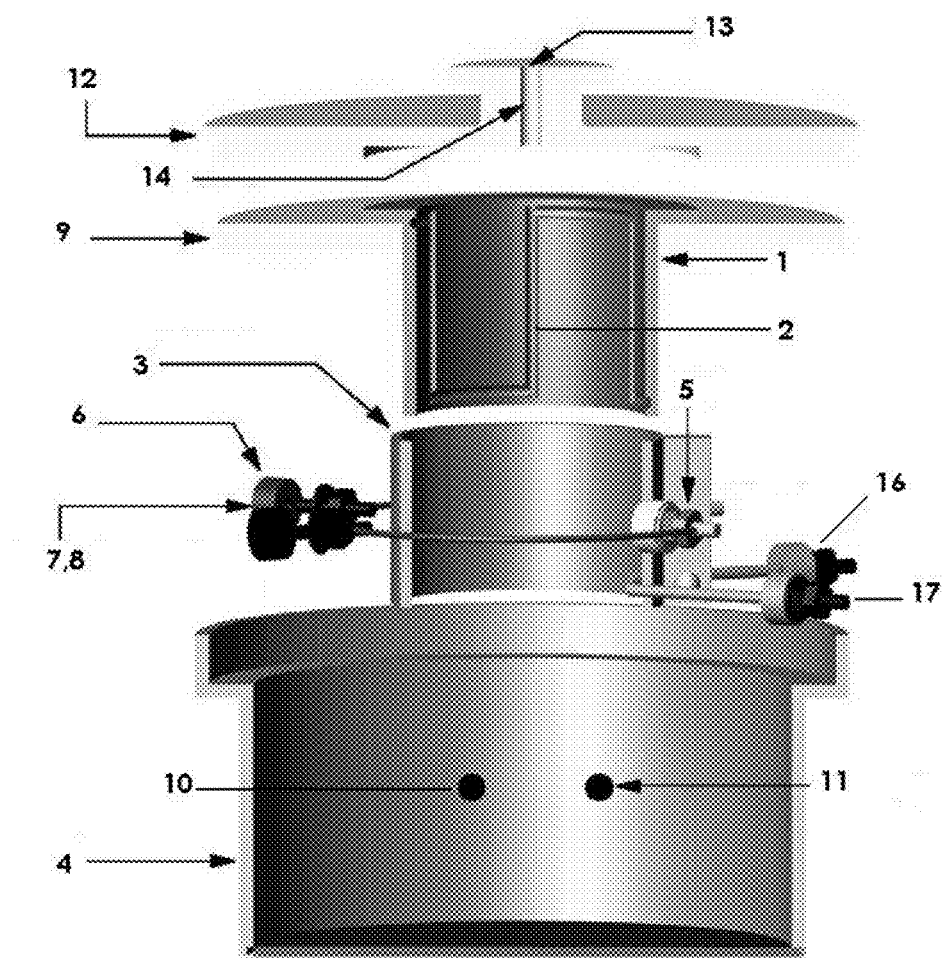
FIG. 1 represents a cross cut of the device for determination of thermal magnitudes of the invention.

The object of the invention is related to a device for the determination of thermal magnitudes fundamentally constituted by a cylinder to hold unaltered samples of soil surrounded by a resistance that creates a radial flow of heat on the soil sample and a refrigeration system based on a heat exchanger in spiral form integrated to the thermal device.

Additionally, another object of the current invention is the application of the invention device to determine the Productive Potential of the Soil (PPS) from the determination of the thermal conductivity of a sample and calculated from an indicator involving synthetic and analytic parameters of soils.

Particularly, another object of the current invention is the application of the invention device for the analysis of the nutritional quality of foods and agro-ecological products from the determination of the thermal conductivity of a sample in the invention device.

DETAILED DESCRIPTION OF THE INVENTION

The current invention refers to a device to determine thermal magnitudes fundamentally constituted by a cylinder to hold unaltered samples of soil surrounded by a resistance that creates a radial flow of heat on the soil sample and a refrigeration system based on a heat exchanger in spiral form integrated to the thermal device.

The thermo-electric technique upon which is based the development of the invention device uses an electric resistance with continuous current as a source of thermal energy that is mostly transferred as heat when the system has an approximately constant volume. The thermal energy dissipated in the resistance (W m$^{-2}$) heats the volume of soil enclosed in the sample holding cylinder according to Fourier's law $$f = \lambda \frac{\delta T}{\delta \vec{s}} = \lambda \vec{V} T$$

where $f_h$ is the density of the flow of thermal energy (W m$^{-2}$) in the direction and sense of the vector: $\vec{s}$; $\nabla T$ is temperature gradient vector (K m$^{-1}$) acting as a heat directing force; and $\lambda$ is the transport coefficient called thermal conductivity (W m$^{-1}$ K$^{-1}$). The minus sign indicates that the flow of thermal energy follows the sense of the decreasing temperatures.

The principle of energy conservation is expressed in the equation of flow conductivity of thermal energy.

$$\frac{\delta Q}{\delta T} = \frac{\delta fh}{\delta \vec{s}} \pm S(\vec{s}, t) \qquad (2)$$

Where Q is the content of thermal energy per unit of volume (J m$^{-3}$); $\delta Q/\delta t$ is the decanting of thermal energy per unit of volume (m$^{-3}$); and of time, t, in seconds (s), and ±S($\vec{s}$.t) is the variation of the stock that is the source of the heat per unit of volume and time (Wm$^{-3}$) within the space considered.

The heat content in the unit of volume varies with temperature, for which the concept of differential calorific capacity can be defined $C_h$ (Jm$^{-3}$ K$^{-1}$)

$$C_h = \frac{dQ}{dT} \qquad (3)$$

Parameters f (W m$^{-1}$K$^{-1}$) and $C_h$(J m$^{-3}$K$^{-1}$) are approximately constant on a uniform soil, but both vary in the same sense with temperature, density or humidity (Farouki, 1986), which suggests its quotient $$D_h = \frac{\lambda}{C_h} \qquad (4)$$

To define the parameter called thermal diffusiveness, $D_h$(m$^2$ s$^{-1}$), which is kept approximately constant with respect to temperature changes.

Combining (1) with (2), dividing by $C_h$ and substituting (3) and (4) we obtain the general equation of the conduction of thermal energy (BAYER, L. D.; GARDNER, W. H.; GARDNER, W. R. Física de suelos. (Traducción de 4. ed. Soil Physiscs, New York: John Wiley and Sons Inc., 1972.). 1 ed. en español. México: Unión Tipográfica Editorial Hispano-Americana U.T.E.H.A., Avenida Universidad, 767, México 12, D. F., p. 529, 1973; HILLEL, D. Fundamentals of soil physics. 1 ed. New York: Academic Press Inc., p. 413, 1980; NERPIN, S. V.; CHUDNOVSKII, A. F. Heat and mass the plant-soil-air system. Ed. A. A. Balkema/Rotterdam, 1985. Russian translations series 29, 355 p.; MUSY, A.; SOUTTER, M. Physique du sol. Presses polytechniques et universitaires romandes, CH 1015-Lausanne, Collection Gérer l'Environnement, 6, p. 335, 1991)

$$\frac{1 \delta Q}{C_h \delta_i} = \qquad (5)$$

$$\frac{1 \delta f_h}{C_h \delta \vec{s}} \pm \frac{1}{C_h} S(\vec{s},t) = \frac{1\delta}{C_h \delta \vec{s}}(\lambda \vec{\nabla} T) \pm \frac{1}{C_h} S(\vec{s},t) = \frac{\lambda}{C_h} \vec{\nabla}^2 T = \frac{1}{C_h} S(\vec{s},t)$$

$$\boxed{\frac{\delta T}{\delta_t} = D_h \vec{\nabla}^2 T \pm \frac{1}{C_h} S(\vec{s},t)} \text{ (Ks}^{-1}\text{)}$$

where $\vec{\nabla}^2 = \vec{\nabla} \times \vec{\nabla}$ is the Laplace operator defined as a scalar product of the gradient operator by itself; T=T(r,t) the absolute temperature in degrees Kelvin (K) at distance r in meters (m) and time t in seconds (s), $D_h$ the heat diffusiveness (m$^2$s$^{-1}$); $C_h$ the differential calorific capacity (Jm$^{-3}$K$^{-1}$) and
S($\vec{s}$, t)/$C_h$ the source obtained by dividing the power per unit of volume (Wm$^{-3}$) by the differential calorific capacity $C_h$(Jm$^{-3}$K$^-$), which defines by unit of section and radius increase (Js$^{-1}$m$^{-2}$m$^{-1}$) a rate of temperature increase in Ks$^{-1}$.

The experimental device (FIG. 1) suggests resolving (5) in cylindrical coordinates (r,φ,z) where r is the radial distance from the linear source of heat, φ is the angle, and z is the azimuthal coordinate and keeping the heat source constant.

$$D_h\left(\frac{\delta^2 T}{\delta r^2} + \frac{1\delta T}{r\delta r} + \frac{1\delta^2 T}{r^2 \delta \varphi^2} + \frac{\delta^2 T}{\delta z^2}\right)\frac{\delta T}{\delta t} = \pm \frac{S}{C_h} \qquad (6)$$

Where sources are expressed in units of differential caloric capacity by the quotient S/$C_h$ Considering, for geometric reasons, that temperature is independent of the height of the cylinder (z) and that it is uniform in its distribution with respect to the angle, φ, and that the source is constant, equation (6) is reduced to the following expression:

$$D_h\left(\frac{\delta^2 T}{\delta r^2} + \frac{1\delta T}{r\delta r}\right)\frac{\delta T}{\delta t} = \pm \frac{T_o}{t} \qquad (7)$$

Which is the equation of the transitory regime of the temperature-time (T,t) pair from (T0.0) to (T,t).

The increase of soil temperature over time from (T0.0) to (T,t) is given by the solution in equation (7) assuming that as of an initial given moment (T=T0 t=0) the source (q) that expels the heat per unit of longitude (z) of the electrical resistance inside the cylinder is constant and the second member T0/t wanes upon increasing t. The solution for (7) is obtained through mathematical procedures to solve the Laplace equation (NERPIN, S. V.; CHUDNOVSKII, A. F. Heat and mass the plant-soil-air system. Ed. A. A. Balkema/Rotterdam, 1985. Russian translations series 29, 355 p.; Jury, W. A. and Roth, K. Transfer functions and solute movement through soil. Theory and applications. 1 ed. Basel: Birkhäuser Verlag Basel, 226 p., 1990) substituting the T(r,t) function for its transformed function $$\vec{T}(p, t) = \int_0^{\infty} e^{-pt} T(r, t) dt \tag{8}$$

For time values $0 \leq t <_{\infty}$ and for values of the conjugated variable (p) within the domain of the existence of the integer, with the initial condition that defines the temperature in the whole domain of integration of the differential equation, a moment adopted as origin of time (t=0)

$$T(r;0) = T_0 \tag{9}$$

And with the outline condition of the physical law of heat conduction (1) in the whole domain of integration and which takes known values just on the surfaces of the border $$\left(\frac{\delta T}{\delta r}\right)_{r=0} = -\left(\frac{f_h}{\lambda}\right)_{r=0} = \frac{q}{\lambda} \tag{10}$$

where q(W m$^2$) is the source expelling the heat per unit of time and surface of the source corresponding to each unit of azimuthal longitude (z=1 m) of the cylinder.

Equation (7) with the transformation (8) and the conditions (9) and (10) turns into the subsidiary equation $$\frac{\delta^2 \vec{T}}{\delta r^2} + \frac{1 \delta \vec{T}}{r \delta r} - q^2 \vec{T} = 0 \tag{11}$$

That is a Bessel equation whose solution is known and found in mathematical tables. Undone the transformation of the solution of (11) results the solution of (7)

$$T - T_0 = \frac{q}{4\pi\lambda}\left[-Ei\left(\frac{r^2}{4D_h t}\right)\right] \tag{12}$$

where Ei (−x) is an exponential whose values are found in mathematical tables.

The exponential may be estimated by a logarithmic function when increasing time and clearing (finding) λ results the following expression (Farouki, O. T. Thermal properties of soils. Trans. Tech. Publications D-3392 Clausthal-Zellerfeld. Germany, Series on Rock and Soil Mechanics v. 11, p. 136, 1986)

$$\lambda = \frac{q}{4\pi(T_2 - T_1)} \ln\left(\frac{t_2}{t_1}\right) \tag{13}$$

Where the thermal conductivity λ is an almost constant parameter in space and time resulting from the proportionality between the increase of temperature $(T_2-T_1)$ and of the logarithm of time ($1nt_2-1nt_1$). The value of q is obtained from the intensity, I, of the current in amperes (A) and the resistance, R, in ohms (Ω) divided by the longitude, z (m), of the cylinder or of the intensity, I, and the difference of potential given by Ohm's law (V=I.R) between the extremes of the resistance with equal longitude as the cylinder.

With reference to FIG. 1, it may be appreciated that the device for thermo-electric measurements of the invention is constituted by a copper cylindrical nucleus (1) with a refrigerant system (2) holder for unaltered soil samples, which is surrounded by an electrical resistance (3) that generates a radial flow of heat on the soil sample through a continuous current produced by a power source. The sample holding cylinder (1) is thermally isolated within a cylinder (4) that serves as support for the setup. The total diameter of the device for thermo-electric measurements may vary in the range of 10 to 20 cm, preferably, between 11 and 13 cm and its height is between 15 and 25 cm, preferably, between 17 and 20 cm in which determinations can be done of unaltered soil samples at any depth in 5-cm cylindrical nuclei (both in height as in diameter).

The electrical resistance (3) surrounding the external part of the copper holder cylinder (1) with refrigerant system (2), has two receptor terminals (5,6) to which are connected two lines of electrical cable (7,8) connected to the power source. The cylinder (1) is isolated by means of a ring (9) elaborated from thermal isolating material, supported by the external cylinder (4) to which the two terminals are canalized (10,11) to receive the two male connectors from the feeding source.

On the upper part, the copper holding cylinder (1) with refrigerant system (2) is isolated by a lid (12) made of thermal isolating material, which serves as a guide to locate a thermopair (20) inside the soil sample (M), through a concentric orifice (13) provided on the isolating lid (12) and a guide of the thermocouple (14) extended transversely.

Figure 2:
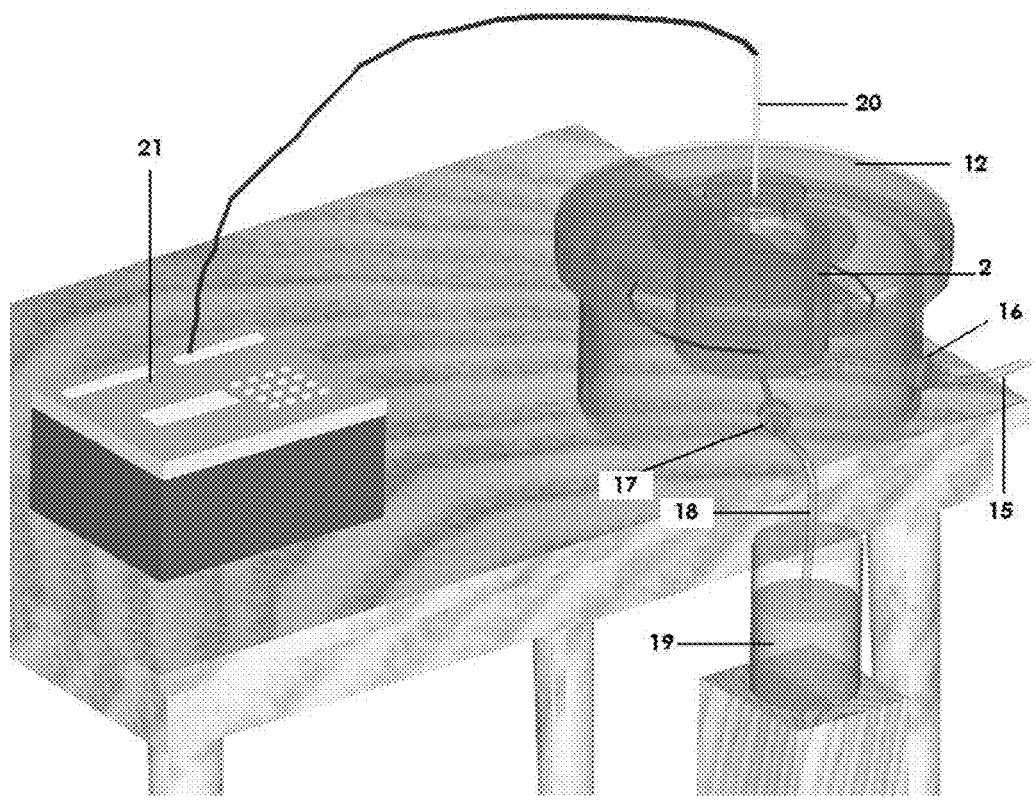
FIG. 2 represents the device for determination of thermal magnitudes of the invention coupled to the system of data storage and to the source that feeds the refrigeration system.

For the operation of the heat exchanger (2), a hose is connected (15) from a water source to a point of connection of entry to the probe constituted by a joint fitting (16) and the exit (17) is connected to a hose (18) that flows into a tank (19). FIG. 2 presents the invention device connected to a thermocouple (20) to acquire temperature data and a device for data storage (21) that registers data onto a PC.

The novel system of the invention device permits making quick measurements of the thermal conductivity in soil samples, storing data, cooling the system, and calibrating the device for the next measurement in an average of 10 minutes.

The method for the determination of the thermal conductivity is developed by placing the carrying cylinder (1) of the device for thermo-electric measurements, the unaltered soil sample (M), in which the thermopair is introduced (20) exactly in the center, for data registry. Then the terminals are connected (10-11) to the electrical connectors with its respective cables coming from the power source to supply electrical current to the resistance (3) through the lines (7,8) of electrical cable. The electric current and the difference of potential are registered in multimeters connected in series and in parallel, respectively.

The materials employed for the construction of the device for thermo-electric measurements according to the invention, come determined in conformity with the corresponding technical requirements, as described herein: the carrying cylinder (1) is elaborated from copper, this material was selected because it is a good heat conductor, the resistance (3) is conformed by Cantal wire covered with stainless steel, while the isolating ring (9) and the lid (12) are elaborated with thermal isolating material based on acrylic.

The device for thermo-electric measurements of the invention is turned on when applying a continuous current that circulates through the resistance (3), the thermal energy dissipated by the resistance generates a heat flow on the soil that permits determining the thermal conductivity of such, furnishing information on the Productive Potential of the Soil or of its energetic reserve, calculated from an indicator that involves synthetic and analytic parameters of the soils. Thermal conductivity is a synthetic parameter of the soil related to its energetic state. The effect of farming the soil bears an impact upon the thermal conductivity and, hence, on the energetic state of the soil.

The determination of the Productive Potential of the Soil (PPS) can be represented in maps that show the spatial variability of the energetic reserve of the soil and, thus, it is possible to design a differential fertilization plan, which increases efficiency and saves costs in fertilization.

Also surprisingly, it has been shown that a device for thermo-electric measurements of this type can be used for the analysis of the nutritional quality of foods and to identify the quality of agro-ecological or organic products.

The following experiments were developed to evaluate the invention device in determination processes of the Productive Potential of the Soil (Experiment 1) and analysis of the organic quality of foods and agricultural products (Experiment 2).

EXAMPLE 1

Determination of the Productive Potential of the Soil

The Productive Potential of the Soil (PPS) is a representative index of the welfare state of the soil. The indices to determine the Productive Potential of the Soil were classified into synthetic, such as, the thermal conductivity of the soil, electrical resistivity ($\rho$), Impedance ($\Omega$), and respirometry on the field ($CO_2/m^2$); and analytical through apparent density (Ad), microbial activity (MA), percentage of macropores (% Macro), gravimetric humidity (% W), and the percentage of sand (% Sand), determined in the Laboratory of Environmental Physics at Universidad del Valle.

The process to determine the Productive Potential of the Soil (PPS) includes the stages of:
a) Initial sampling of the soil.
b) Determination of the thermal conductivity in soil samples through the invention device.
c) Determination of electrical Resistivity ($\Omega$.m), Organic Matter (%), apparent Density (g/cm$^3$), Macro-pores (%), Microbial Activity ($\mu gC$-$CO_2$/gSS), Ratio of ((Ca+Mg)/K)—Hydrogen Potential (HP), Interchangeable Bases (Cmol/kg)—CIC (Cmol/kg) in soil samples through techniques suitable for each variable.
d) Elaboration of the map of Productive Potential of the Soil according to the ratio of the thermal conductivity and other variables in soil samples.
e) Differential fertilization of the area.

Figure 3:
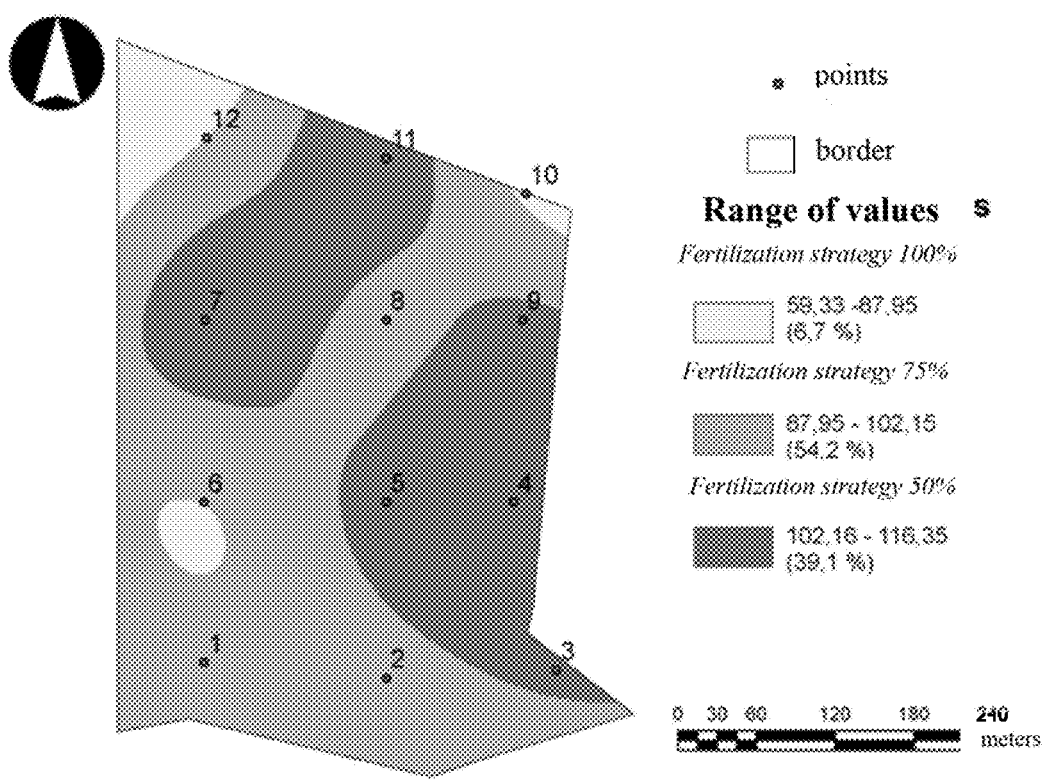
FIG. 3 represents the map of differential fertilization obtained through the process of determination of the Productive Potential of the invention for a sugar cane plantation in Valle del Cauca.

Through this process, the Determination of the Productive Potential was performed for a sugar cane plantation in Valle del Cauca, obtaining the values for thermal conductivity in 12 soil samples from the farming area through the invention device and elaborating the differential fertilization map for the sugar cane plantation (FIG. 3). Three fertilization strategies are established from this map depending on the welfare state of the soil, the strategy of 100% fertilization representing 6.7% of the area of study, the strategy of 75% fertilization applied to 54.2% of the area, and the strategy of 50% fertilization representing 39.1% of the farming area.

Experiences carried out applying the process of the invention at Ingenio Central Castilla have permitted reducing fertilization costs by 23%, where the investment per Ha of fertilization amounts to Col$980000 with direct sowings of 11.000 Ha. Hence, the process of the invention to establish the Productive Potential of the Soil (PPS) through the Determination of the thermal conductivity in the invention device results of vital importance to increase productivity and competitiveness in the region's agricultural sector.

EXAMPLE 2

Evaluation of the Quality of Agro-Ecological Products

The process for analysis of the nutritional quality of foods and agro-ecological products from the determination of the thermal conductivity of a sample in the invention device is based on the existing relationship between thermal conductivity and organic materials, which permit associating the thermal behavior of the products as a quality indicator.

The process to analyze the nutritional quality of foods and agro-ecological products of the invention includes the sampling stages of the agro-ecological product or food and determination of the thermal conductivity in the samples of the product through the invention device.

Figure 4:
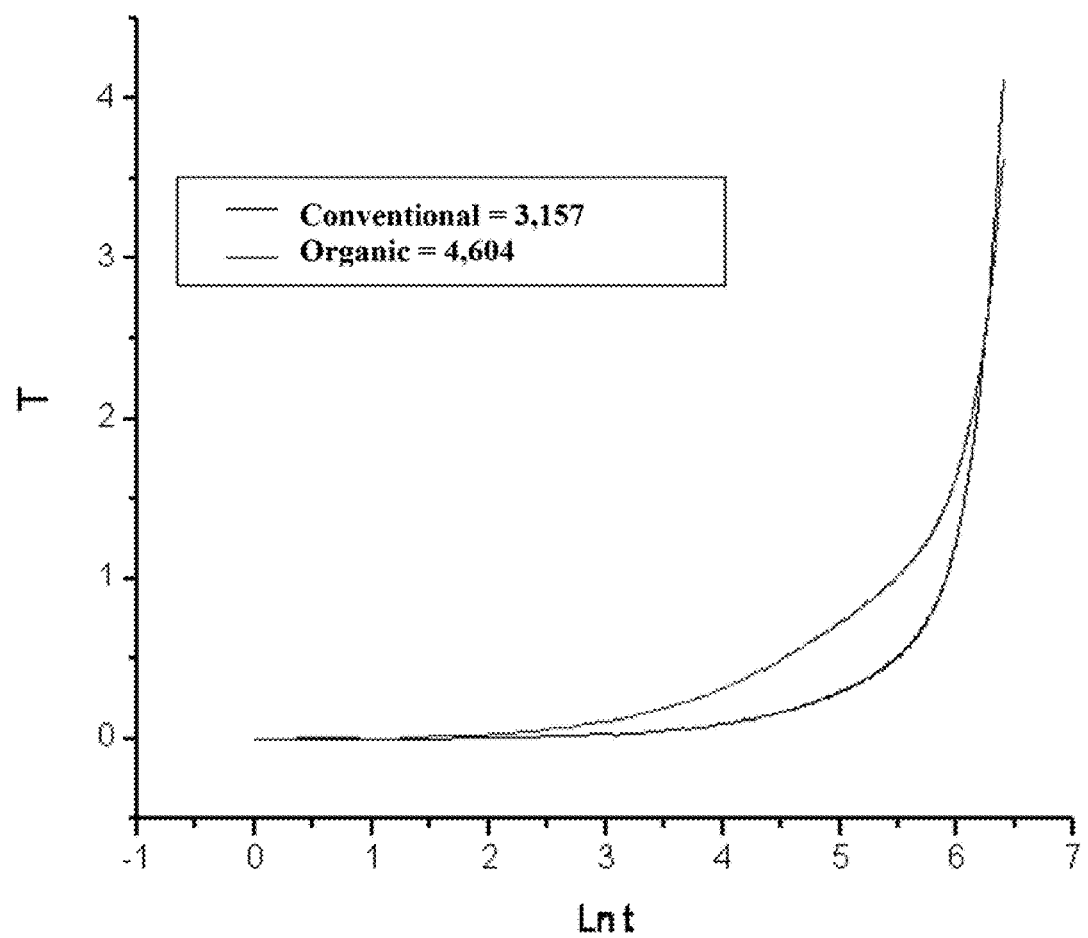
FIG. 4 presents the comparative graphics for thermal conductivity of organic coffee and conventional coffee obtained through the application of the invention device.
Figure 5:
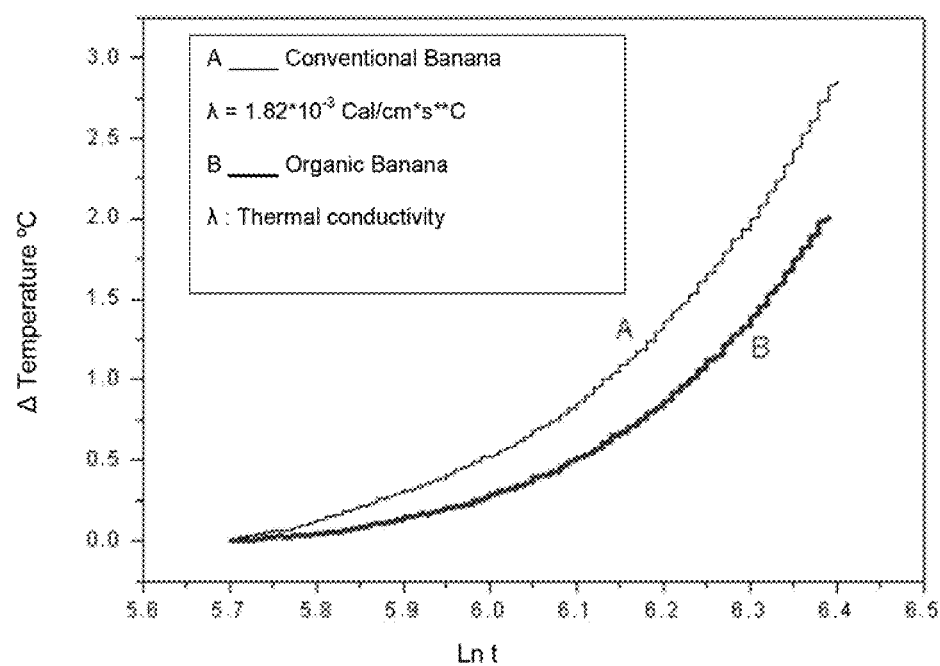
FIG. 5 presents the comparative curves of thermal conductivity for samples of organic banana and conventional banana obtained through the application of the invention device.

The tests were held comparing organic coffee to conventional coffee and organic banana to conventional banana, the results obtained are shown in FIGS. 4 and 5. These graphics show the marked differences in thermal conductivity for conventional and organic products, for which the invention device for thermo-electric measurements may be used in the evaluation process of the quality of organic products and may be considered a quantitative factor to obtain the green seal in ecological export products.

The invention claimed is:
1. A device for measuring thermo-electric values for use in determining thermal conductivity of a sample, the sample being soil, the device comprising:
  a copper cylindrical nucleus for receiving the soil;
  an electrical resistance surrounding at least a portion of the cylindrical nucleus, the electrical resistance being configured to generate a flow of heat on the soil;
  a cylindrical support for thermally insulating and supporting the cylindrical nucleus;
  a thermopair element insertable into at least a portion of the cylindrical nucleus, the thermopair element being configured to measure thermo-electric data of the soil;
  a first conduit configured to permit water to enter at least a portion of the device;
  a water source connected to the first conduit via a hose;
  a second conduit configured to permit water to exit at least a portion of the device;
  a reservoir connected to the second conduit via a hose, the reservoir being configured to receive and hold water, the reservoir being spaced-apart from the water source; and
  a data storage device connected to the thermopair element,
  wherein thermal conductivity of the soil is determined based on the data.

2. The device according to claim 1 wherein said copper cylindrical nucleus includes an integrated refrigerant system.

3. The device according to claim 1 wherein said electrical resistance includes receptor terminals.

4. The device according to claim 3 wherein the receptor terminals are connected to electric source means.

5. The device according to claim 3 wherein said receptor terminals are connected to electric source means.

6. The device according to claim 1 wherein the cylindrical support is isolated by a ring formed of a thermal isolating material.

7. The device according to claim 1 wherein said cylindrical support includes receptor terminals.

8. The device according to claim 1 wherein said copper cylindrical nucleus is isolated by a lid made of thermal isolating material.

9. The device according to claim 8 wherein said lid includes a concentric orifice.

10. The device according to claim 1 wherein said thermopair element includes guide means which are extended transversally.

11. The device according to claim 1 wherein the device further comprises an input joint fitting and an output joint fitting.

12. The device according to claim 1 wherein said data storage device registers information in a data processing unit.

13. The device according to claim 1 wherein a total diameter of the device to determine thermal conductivity is within the range of 10 to 20 cm.

14. The device according to claim 1 wherein determinations of thermal conductivity are made of unaltered soil samples from any depth in 5-cm cylindrical nuclei both in height and diameter.

15. The device according to claim 1 wherein the copper cylindrical nucleus is hollow.

16. The device according to claim 1 further comprising:
a lid attached to an upper end of the copper cylindrical nucleus, the lid including an orifice extending transversely through the lid,
wherein the thermopair element is insertable into the orifice of the lid for measuring thermo-electric data of the soil.

17. A method for determining the thermal conductivity of a sample using the device of claim 1 comprising:
(a) placing the sample in the copper cylindrical nucleus;
(b) introducing the thermopair element exactly in the center of the sample;
(c) applying an electrical current to the electrical resistance;
(d) measuring a temperature, an electric current and a difference of potential in the sample; and
(e) determining the thermal conductivity of the sample.

18. A method for determining a nutritional quality of foods and agro-ecological products, the method comprising determining thermal conductivity a food or agro-ecological product sample using the device of claim 1.

* * * * *